(12) United States Patent
Castro

(10) Patent No.: US 11,413,073 B2
(45) Date of Patent: Aug. 16, 2022

(54) SURGICAL FASTENER

(71) Applicant: Blue Sky Technologies, LLC, Louisville, KY (US)

(72) Inventor: Frank Castro, Louisville, KY (US)

(73) Assignee: BLUE SKY TECHNOLOGIES, LLC, Louisville, KY (US)

( * ) Notice: Subject to any disclaimer, the term of this patent is extended or adjusted under 35 U.S.C. 154(b) by 67 days.

(21) Appl. No.: 17/079,429

(22) Filed: Oct. 24, 2020

(65) Prior Publication Data

US 2021/0244455 A1 Aug. 12, 2021

Related U.S. Application Data

(60) Provisional application No. 62/975,248, filed on Feb. 12, 2020.

(51) Int. Cl.
*A61B 17/86* (2006.01)
*A61B 17/70* (2006.01)
*A61B 17/16* (2006.01)
*A61B 17/84* (2006.01)

(52) U.S. Cl.
CPC .......... *A61B 17/7055* (2013.01); *A61B 17/16* (2013.01); *A61B 17/7035* (2013.01); *A61B 17/84* (2013.01); *A61B 17/8605* (2013.01); *A61B 17/8625* (2013.01); *A61B 17/8635* (2013.01); *A61B 2017/8655* (2013.01)

(58) Field of Classification Search
CPC ............ A61B 17/8625; A61B 17/8635; A61B 17/8095; A61B 17/846; A61B 17/686; A61B 2017/0647
See application file for complete search history.

(56) References Cited

U.S. PATENT DOCUMENTS

| | | | |
|---|---|---|---|
| 3,887,186 A | 6/1975 | Matlock, Jr. | |
| 7,922,720 B2 | 4/2011 | May et al. | |
| 8,100,972 B1 | 1/2012 | Bruffey et al. | |
| 8,545,562 B1 | 10/2013 | Materna et al. | |
| 9,421,112 B2 | 8/2016 | Bal et al. | |
| 10,159,516 B2 | 1/2018 | Tan | |
| 10,405,872 B2 | 9/2019 | Victor et al. | |
| 2002/0120274 A1* | 8/2002 | Overaker | A61F 2/30756 606/908 |
| 2003/0036801 A1* | 2/2003 | Schwartz | A61L 27/3654 606/907 |
| 2009/0265006 A1 | 10/2009 | Seifert et al. | |

\* cited by examiner

*Primary Examiner* — Olivia C Chang
(74) *Attorney, Agent, or Firm* — Business Patent Law, PLLC

(57) ABSTRACT

A surgical fastener provided with a curved cutter, an anterior wedge-like tip and a surgeon facing end. Among other things, the surgical fastener's cutter can cut bone or other tissue.

19 Claims, 2 Drawing Sheets

SURGICAL FASTENER

PRIORITY

Applicant claims the benefit of U.S. Provisional Application No. 62/975,248—Surgical Fastener—filed on Feb. 12, 2020.

BACKGROUND OF THE INVENTION

A. Field of the Invention

The present invention is surgical fastener provided with slanted cutting edges, an anterior wedge-like tip, a front end and a surgeon facing end. In select preferred embodiments, a head extends from the surgeon facing end. The head can be fixed or polyaxial. Except for the head, the surgical fastener is threadless.

B. Description of the Previous Art

Any discussion of references cited in this Description of the Previous Art merely summarizes the disclosures of the cited references and Applicant makes no admission that any cited reference or portion thereof is relevant prior art. Applicant reserves the right to challenge the accuracy, relevancy and veracity of the cited references.

References that may indicate a state-of-the-art include: 1) U.S. Pat. No. 3,887,186-Matlock Jr. discloses a broadhead; 2) U.S. Pat. No. 8,100,972-Bruffey, et al. discloses a spinal cage having deployable member; 3) U.S. Pat. No. 8,545,562-Materna et al.; 4) U.S. Pat. No. 9,421,112-Bal, et al. discloses a fixation system for spinal cages; 5) U.S. patent Ser. No. 10/159,516-Tan discloses an interchangeable orthopedic blade; 6) U.S. patent Ser. No. 10/405,872-Victor, et al.; 7) US Published Patent Application 20090265006-Seifert, et al. discloses a lateral spinous process spacer; and U.S. Pat. No. 7,922,720—May, et al. discloses an orthopaedic cutting instrument and method.

Among other things, none of the above listed references, alone or in combination, disclose a surgical fastener comprising: a) a wedge-like tip positioned at a first lengthwise end of a cutter; the wedge-like tip integral with the cutter and of lesser width than the first lengthwise end of the cutter such that the wedge-like tip is adapted to engage a joint space or a portion of a surgically created cavity or the joint space; b) a longitudinal axis (X-X) extending through the wedge-like tip, the anterior edge and a surgeon facing end of the cutter; c) the cutter further comprising a first section and a second section adapted to cut biological tissue; the first and second sections positioned on opposed sides of the longitudinal axis (X-X); each section extending the length of the cutter from the first lengthwise end to the surgeon facing end, wherein the first and second sections are adapted to cut radially relative to the longitudinal axis (X-X); d) the first section comprising a greater width proximate the surgeon facing end and a slanted first cutting straight edge distal from the longitudinal axis (X-X) slanted at an angle of from about 30 degrees to about 70 degrees relative to the longitudinal axis (X-X); and e) the second section comprising a greater width proximate the surgeon facing end and a slanted second cutting straight edge distal from the longitudinal axis (X-X) slanted at an angle of from about 30 degrees to about 70 degrees relative to the longitudinal axis (X-X), wherein after insertion through a surgical incision, engagement of the joint space or a portion of the surgically created cavity or the joint space by the surgical fastener and subsequent rotation of approximately 90 degrees of the cutter relative to an engagement point of the wedge-like tip, the surgeon facing end of the surgical fastener is positioned to resist pull out of the surgical fastener from the joint space or a portion of the surgically created cavity or the joint space.

SUMMARY OF THE INVENTION

Successful fusion of a joint or broken bone is directly correlated to the construct rigidity surrounding the area of interest. Current spinal instrumentation relies on screws being anchored into bone and rods connecting to these anchors. Loosening of current constructs occurs primarily at the bone-anchor interface. Toggling of the screws can allow for enlargement of the insertion pathway. As the diameter of the insertion pathway increases, there is greater risk of the screw backing out and construct failure. The current invention can be utilized for arthrodesis procedures of the cervical, thoracic and lumbar spine, as well as the sacroiliac joint or other similar joints.

The biomechanical strength of traditional threaded fixation screws is dependent upon several design characteristics. Larger diameter screws are stronger and more difficult to extract due to increased surface area (friction). The thread pitch, or difference between the inner diameter and the outer diameter, also influences resistance to pull out or back out. The larger the pitch the greater the resistance to pull out. Biomechanical studies have demonstrated that the volume of bone between screw threads can influence the screw's resistance to pull out. Those skilled in the art recognize that the type and quality of bone are important variables influencing resistance to pull out. Patients with osteoporotic bone have significantly less dense bone than patients with normal bone densities. The contribution of the cancellous bone between the screw threads in patients with osteoporosis is less than patients of normal bone density. In some osteoporotic patients, the screw's fixation strength and resistance to pull out can be determined by the volume of cortical bone in one or two threads of a traditional fixation screw.

Long surgical constructs, such as those used for scoliosis or deformity correction surgery, are often anchored into the sacrum or ilium. These constructs are usually anchored with a large diameter threaded screw. The biophysical forces transmitted to these implanted screws can lead to loosening, construct failure, pain and additional revision surgery.

Many of traditional surgical screws include thread lengths of one to two millimeters that determine the screw's fixation strength. The current surgical fastener provides a potential fixation surface area of from about three to about ten times more than traditional fixation screws. In use, the potential surface area of the surgical fastener is generally juxtaposed the cortical bone—the patient's strongest bone. The current invention can be provided with surface treatments and apertures that can encourage bone ingrowth, long-term construct stability and arthrodesis.

Unlike other joint implants, among other things, the present surgical fastener can include slanted cutting edges. Such structures can cut bone and other tissues. Depending on surgical requirements, the surgical fastener can be anchored into the cervical spine, sacrum, the ilium, posterior occiput or the sacroiliac joint.

Preferred embodiments of the surgical fastener, among other things, can include an anterior edge wedge-like tip, cutter and head.

The anterior wedge-like tip can separate surfaces or a joint, such as the sacroiliac joint or posterior cervical joint or the frontal edge can cut cortical bone. When rotated, the surgical fastener can be adapted to cut cartilage, cortical bone or other tissues that can provide exposure of bone to another bony surface. Exposing two bony surfaces can increase the probability the bony surfaces of the surfaces uniting into a solid fusion. The cutter may facilitate reapproximation of two joint surfaces that have experienced a distractive deformity from trauma or tumor. Prior to cutting through the first articular surface, the cutter can guide the bone back towards its anatomic position. Once the cutter crosses both articular surfaces, forward pressure on the cutter compresses the two surfaces and the curved cutter can prevent retropulsion. When the cutter is placed across a joint, it may also facilitate fusion by exposing a conduit for bone to form across the joint. When the cutter is positioned completely across a joint, it may compress the articular or bony surfaces. Such imposed motion limitation may result in joint ankylosis.

Among other things, the surgical fastener's head can: limit the depth the fastener can be inserted through the incision into the surgically created cavity or joint space; be connected with other surgical apparatus, such as, rods, plates or other fixation devices; and relative to a headless screw, apply increased torque to the cutter.

Intentional or unintentional rotation of threaded devices can lead to displacement of the device into or towards an undesirable location resulting in damage or dysfunction to either a nerve or blood vessel. Those skilled in the art recognize that expulsion of a surgical screw results in an unstable screw that can increase the risk of non-fusion or spinal deformity. Among other things, the surgical fastener can be provided with a head of sufficient area to prevent over-insertion into the surgically created cavity or joint space. Depending on medical and/or surgical parameters, the current invention can be adapted to either compress or distract a joint. By way of illustration, when distraction of the posterior cervical facet joint occurs, the adjacent neuroforamin is enlarged and indirect decompression of the exiting nerve root can occur.

Subsequent to insertion into a surgically created cavity or joint space with adequate outward tissue remaining proximate the insertion point, rotating the surgical fastener from about 30 degrees to about 150 degrees can improve the surgical fastener's resistance to pull out forces.

An aspect of the present invention is to provide a surgical fastener.

Still another aspect of the present invention is to provide a surgical fastener with a wedge-like tip and a head opposite the wedge-like tip.

It is yet another aspect of the present invention to provide a surgical fastener with either a fixed head or a polyaxial head.

Still another aspect of the present invention is to provide a surgical fastener with a receiver adapted to receive an apparatus distinct from the surgical fastener.

It is still another aspect of the present invention to provide a surgical fastener including first and second sections with cutting edges to cut the biological structure or tissue.

Yet still another aspect of the present invention is to provide a surgical fastener with a cutter including first and second sections where each section includes a slanted cutting edge.

Still another aspect of the present invention is to provide a surgical fastener where only the head is provided with threads.

A preferred embodiment of the current invention can be described as a surgical fastener comprising: a) a wedge-like tip positioned at a first lengthwise end of a cutter; the wedge-like tip integral with the cutter and of lesser width than the first lengthwise end of the cutter; the anterior edge of the wedge-like tip parallel to the lengthwise first end of the cutter such that the wedge-like tip is adapted to engage a joint space or a portion of a surgically created cavity or the joint space; b) a longitudinal axis (X-X) extending from the wedge-like tip through the cutter and a receiver positioned in a surgeon facing end of the cutter, wherein the receiver is adapted to receive an apparatus distinct from the surgical fastener; c) the cutter further comprising a first section and a second section adapted to cut biological tissue; the first and second sections positioned on opposed sides of the longitudinal axis (X-X); each section extending the length of the cutter from the first lengthwise end to the surgeon facing end, wherein the first and second sections are adapted to cut radially relative to the longitudinal axis (X-X); d) the first section having a greater width proximate the surgeon facing end; the first section further comprising a slanted first cutting straight edge distal from the longitudinal axis (X-X); the slanted first cutting straight edge slanted at an angle of from about 30 degrees to about 70 degrees relative to the longitudinal axis (X-X); and e) the second section having a greater width proximate the surgeon facing end; the second section further comprising a slanted second cutting straight edge distal from the longitudinal axis (X-X); the slanted second cutting straight edge slanted at an angle of from about 30 degrees to about 70 degrees relative to the longitudinal axis (X-X), wherein rotation of the surgical implant connects the surgical implant to the joint space or a portion of the surgically created cavity or the joint space.

Another preferred embodiment of the current invention can be described as a surgical fastener comprising: a) a wedge-like tip positioned at a first lengthwise end of a cutter; the wedge-like tip integral with the cutter and of lesser width than the first lengthwise end of the cutter; the anterior edge of the wedge-like tip parallel to the lengthwise first end of the cutter such that the wedge-like tip is adapted to engage a joint space or a portion of a surgically created cavity or the joint space; b) a longitudinal axis (X-X) extending from the wedge-like tip through the cutter and a head connected with a surgeon facing end of the cutter, wherein the head is adapted to receive an apparatus distinct from the surgical fastener; c) the cutter further comprising a first section and a second section adapted to cut biological tissue; the first and second sections positioned on opposed sides of the longitudinal axis (X-X); each section extending the length of the cutter from the first lengthwise end to the surgeon facing end, wherein the first and second sections are adapted to cut radially relative to the longitudinal axis (X-X); d) the first section having a greater width proximate the surgeon facing end; the first section further comprising a slanted first cutting straight edge distal from the longitudinal axis (X-X); the slanted first cutting straight edge slanted at an angle of from about 30 degrees to about 70 degrees relative to the longitudinal axis (X-X); and e) the second section having a greater width proximate the surgeon facing end; the second section further comprising a slanted second cutting straight edge distal from the longitudinal axis (X-X); the slanted second cutting straight edge slanted at an angle of from about 30 degrees to about 70 degrees relative to the longitudinal axis (X-X), wherein rotation of the surgical implant connects the surgical implant to the joint space or a portion of the surgically created cavity or the joint space.

Still another preferred embodiment of the current invention can be described as a surgical fastener comprising: a) a wedge-like tip positioned at a first lengthwise end of a cutter; the wedge-like tip integral with the cutter and of lesser width than the first lengthwise end of the cutter such that the wedge-like tip is adapted to engage a joint space or a portion of a surgically created cavity or the joint space; b) a longitudinal axis (X-X) extending through the wedge-like tip, the anterior edge and a surgeon facing end of the cutter; c) the cutter further comprising a first section and a second section adapted to cut biological tissue; the first and second sections positioned on opposed sides of the longitudinal axis (X-X); each section extending the length of the cutter from the first lengthwise end to the surgeon facing end, wherein the first and second sections are adapted to cut radially relative to the longitudinal axis (X-X); d) the first section comprising a greater width proximate the surgeon facing end and a slanted first cutting straight edge distal from the longitudinal axis (X-X) slanted at an angle of from about 30 degrees to about 70 degrees relative to the longitudinal axis (X-X); and e) the second section comprising a greater width proximate the surgeon facing end and a slanted second cutting straight edge distal from the longitudinal axis (X-X) slanted at an angle of from about 30 degrees to about 70 degrees relative to the longitudinal axis (X-X), wherein after insertion through a surgical incision, engagement of the joint space or a portion of the surgically created cavity or the joint space by the surgical fastener and subsequent rotation of approximately 90 degrees of the cutter relative to an engagement point of the wedge-like tip, the surgeon facing end of the surgical fastener is positioned to resist pull out of the surgical fastener from the joint space or a portion of the surgically created cavity or the joint space.

DESCRIPTION OF THE PREFERRED EMBODIMENTS

Figure 1:
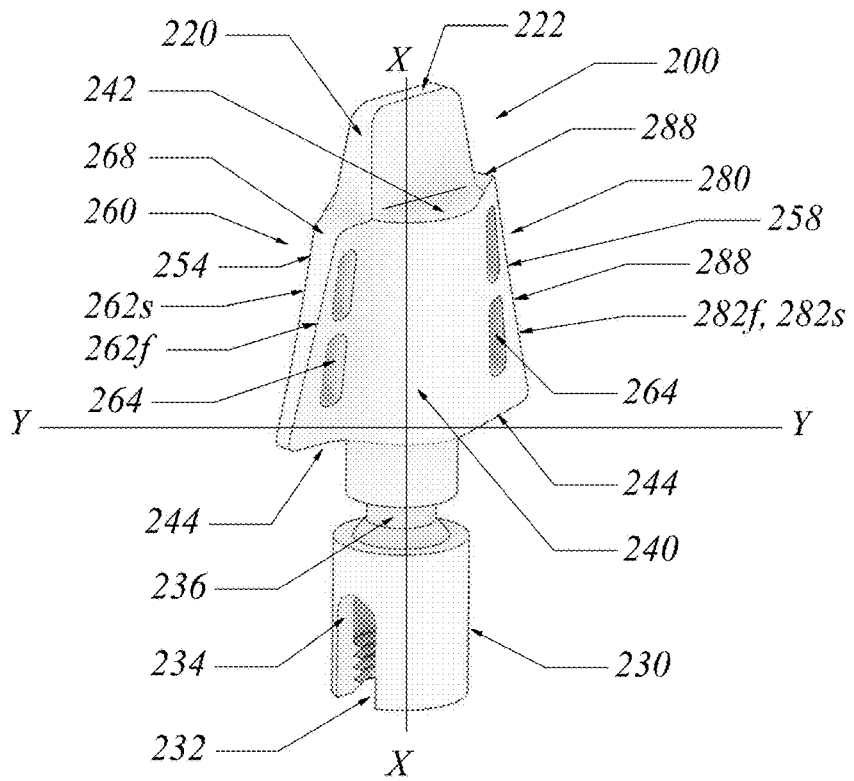
FIG. 1 is a perspective of a preferred embodiment of surgical fastener (200).
Figure 2:
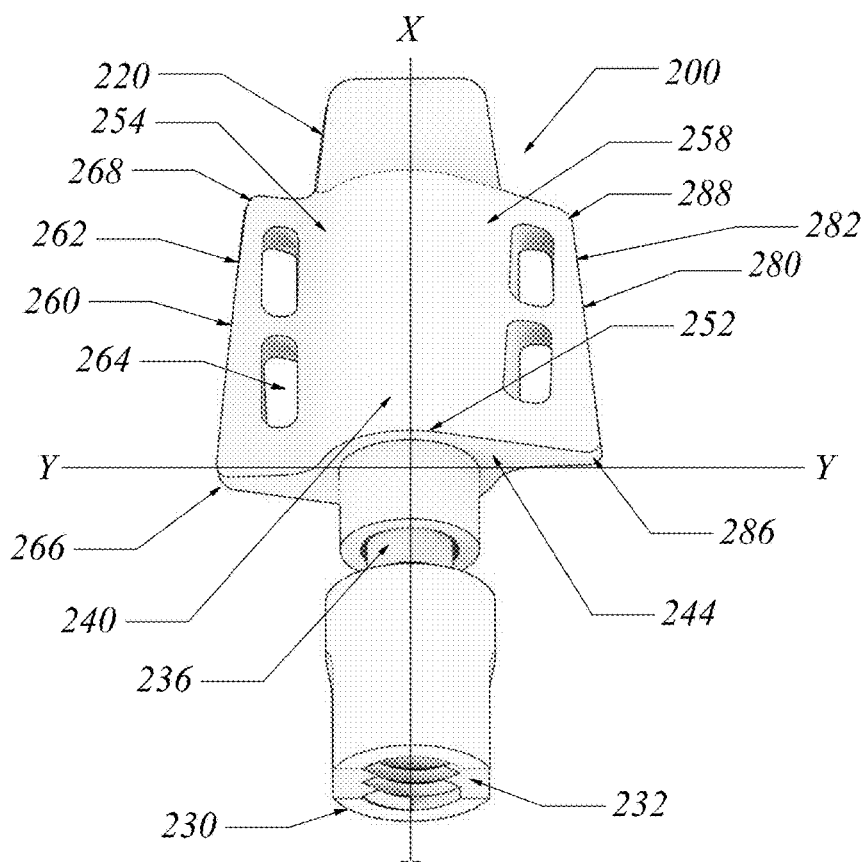
FIG. 2 is a second perspective of the FIG. 1 preferred embodiment of surgical fastener (200) where surgical fastener (200) was rotated approximately 45 degrees.
Figure 3:
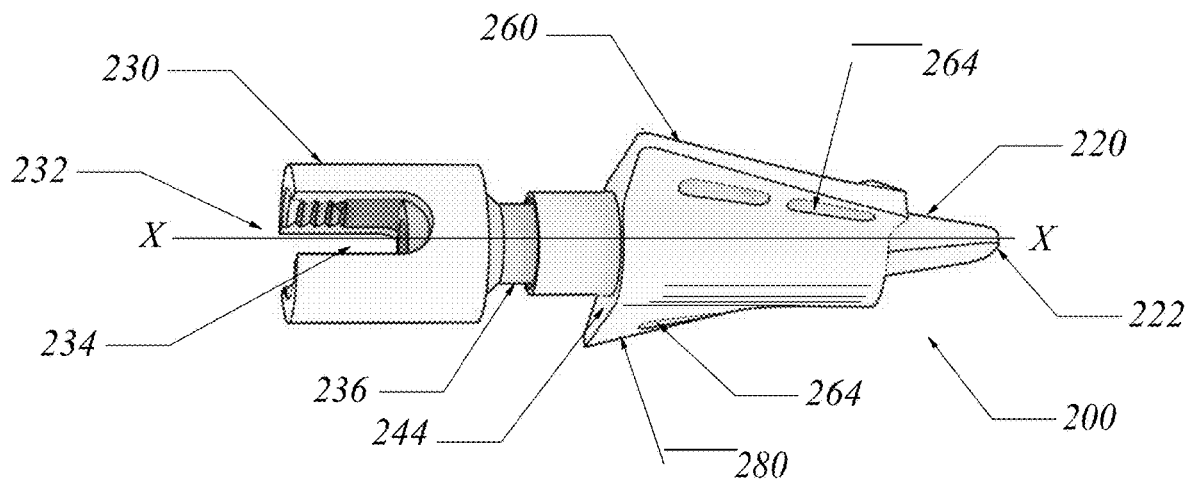
FIG. 3 is a lengthwise perspective of FIG. 1 along longitudinal axis X-X.

Although the disclosure hereof is detailed to enable those skilled in the art to practice the invention, the embodiments published herein merely exemplify the present invention.

As used herein, with respect to the surgical fastener (200): 1) "anterior" of the surgical fastener (200) means the end of the surgical fastener most distant from the surgeon and 2) "posterior or surgeon-facing end" of the surgical fastener (200) means the side of the surgical fastener nearest the surgeon.

In the most general sense, the present invention can result in joint arthrodesis where the surgical fastener is surgically inserted into or across a joint space. Depending on surgical parameters one or more surgical fasteners can be associated with the same surgically created cavity or joint space. The current surgical fastener can be useful for surgeries that can assist in stabilizing injured, deformed and or degenerative joints. Preferred embodiments of the current invention can be employed with ankle, cervical, hand, skull, sacroiliac or other orthopaedic procedures. It appears that the present system is particularly useful for posterior fusions from the occipital region to the pelvis, including the sacroiliac joints. However, the current invention can also be used to fuse the tibia to the talus, the talus to the calcaneus, and metacarpals to the phalanges.

Preferred embodiments of the current surgical fasteners can be manufactured of titanium alloys, stainless steel, non-resorbable polymers or any other composition acceptable in the art. Meeting a long felt but unfilled need in the orthopaedic surgical arts, the novel and unique structures of the present surgical fastener allow the surgical team to, among other things, simplify previous procedures.

The present invention has an anterior side with an anterior wedge-like tip, a cutter and a head, all of which can coincide with the longitudinal axis of the surgical fastener. The anterior edge of the surgical fastener is capable of dissecting through adipose, muscle, bone, and/or joint capsule tissues. The rotatable cutter of the surgical fastener is capable of cutting cartilage and bone and can be associated with the creation of the surgical cavity. Further, the rotatable cutter can morselize bone in preparation for fusion. The combination of the wedge-like tip, rotatable cutter and head of the surgical fastener meet long felt but unfilled needs in the orthopedic surgical arts of, among other things, allowing the surgeon to simplify the previous operating procedures utilized for posterior cervical, sacroiliac, and other joint fusions.

The cutting edges of the surgical fastener are capable of cutting cartilage and bone and can be associated with the creation of the surgical cavity. In select preferred embodiments, cutting edges are distal from the longitudinal axis. Further, the rotatable cutting edges can morselize bone in preparation for fusion. The cutter of the current surgical fastener can be supplied with one or more apertures.

A head can be connected to the surgeon facing side of the cutter. The head can be provided with a receptacle and slots adapted to receive an apparatus distinct from the surgical fastener. Some preferred embodiments include an extender connecting the head to the shaft. Depending on surgical requirements, the head can be either a fixed or polyaxial. And still other embodiments of the cutter can be provided with a receiver adapted to receive an apparatus distinct from the surgical fastener.

The present invention has an anterior side with an anterior wedge-like tip extending from an anterior end of the cutter, slanted cutting edges attached to the cutter and a head attached to the posterior side of the cutter, all of which can coincide with the longitudinal axis of the surgical fastener. The anterior edge of the surgical fastener is capable of dissecting through adipose, muscle, bone, and/or joint capsule tissues. However, within the scope of the current invention, the anterior edge can be dull or sharp. The rotatable cutter is adapted to cut radially in either the clockwise, counterclockwise or both directions.

FIGS. 1-4 are perspectives of surgical fastener (200). Among other things, surgical fastener (200) includes wedge-like tip (220), head (230), cutter (240), first cutting edge (260) and second cutting edge (280). In select preferred embodiments of the cutter (240), first and second cutting edges (260, 280) of first and second sections (254, 258) are straight and slanted relative to longitudinal axis (X-X). First cutting edge (260) can be provided with opposed first and second cutting faces (262f, 262s) adapted to cut radially in either a clockwise or counter clockwise direction or both directions. Select preferred embodiments of first cutting edge (260) can include only a single cutting face. Second cutting edge (280) can be provided with opposed first and second cutting faces (282f, 282s) adapted to cut radially in either a clockwise or counter clockwise direction or both directions. Select preferred embodiments of second cutting edge (280) can include only a single cutting face.

Wedge-like tip (220) is positioned at a first lengthwise end (242) of cutter (240). The wedge-like tip (220) is adapted to engage a portion of a surgically created cavity or a joint space (not shown). Depending on surgical parameters, anterior edge (222) of wedge-like tip (220) can be either dull or sharp.

Head (230) is connected to posterior end (244), opposed from anterior or first end (242) of cutter (240). Head (230) is provided with receptacle (232) adapted to receive an apparatus (not shown) distinct from the surgical fastener (200). Receptacle (232) can be provided with one or more slots (234). Examples of apparatus received by receptacle (232) include insertion drivers that can advance the surgical fastener into or across a joint space, rods used to connect fasteners positioned at other spinal levels, and removal tools if surgical revision is required. Preferred embodiments of the current surgical fastener (200) can include fixed or polyaxial heads. When a polyaxial head (230) is utilized, select preferred embodiment of the current invention can be provided with extender segment (236) extending from polyaxial head (230) and connected to surgeon facing side (244) of cutter (240). Extender segment (236) can expand the multiplanar range of polyaxial head (230).

Figure 4:
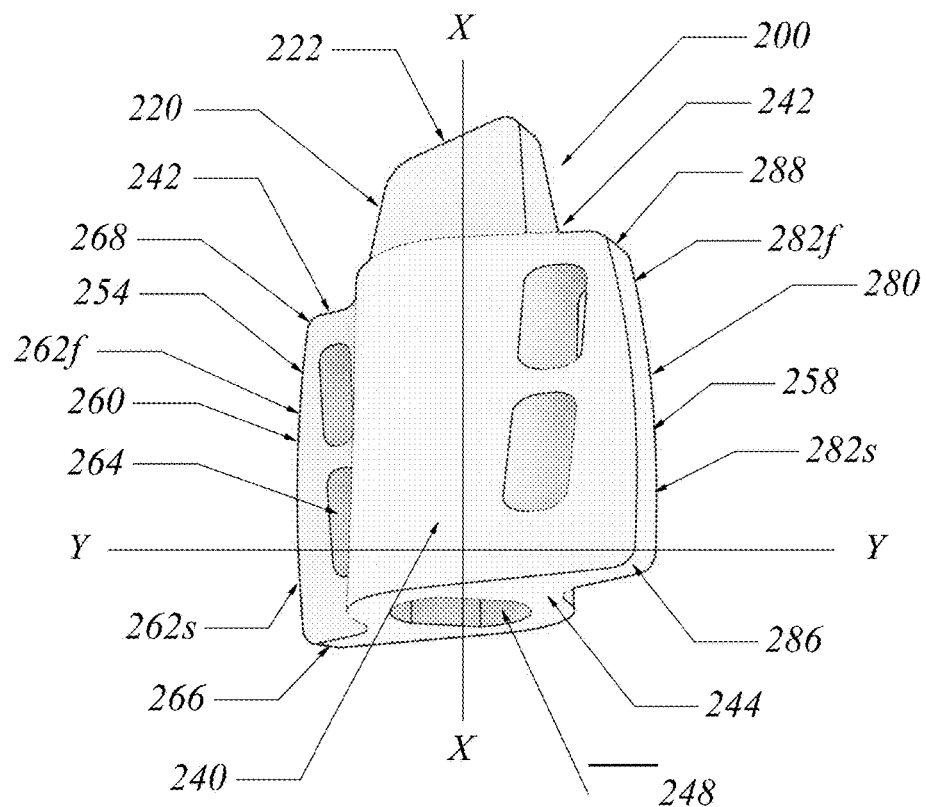
FIG. 4 is a perspective of second end (244) of cutter (240) including a receiver (248).

As shown in FIG. 4, in select preferred embodiments, second end (244) of cutter (240) can be provided with receiver (248) to receive an apparatus distinct from the surgical fastener (200). Use of receiver (248) can eliminate the use of head (230) in operation of the surgical fastener (200).

With a view toward FIGS. 1-4, first cutting edge (260) is attached obliquely to cutter (240) along a first slope of from about 30 about 70 degrees relative to longitudinal axis X-X. A first width (266) of the first cutting edge (260) is greater proximate the posterior end (244) of cutter (240) than a second width (268) proximate the anterior end (242) of cutter (240). First cutting edge (260) can be provided with opposed first and second cutting faces (262f, 262s) adapted to cut radially in either a clockwise or counterclockwise direction or both directions. Select preferred embodiments of first cutting edge (260) can include only a single cutting face.

Second cutting edge (280) is attached obliquely to cutter (240) along a second slope of from about 30 about 70 degrees relative to longitudinal axis X-X. A first width (286) of the second cutting edge (280) is greater proximate the posterior end (244) of cutter (240) than a second width (288) proximate the anterior end (242) of cutter (240). Second cutting edge (280) can be provided with opposed first and second cutting faces (282f, 282s) adapted to cut radially in either a clockwise or counter clockwise direction or both directions. Select preferred embodiments of second cutting edge (280) can include only a single cutting face.

Within the scope of the current invention, preferred embodiments of cutter (240) can be provided with one or more apertures (264) located in the first section (254) and the second section (258).

After insertion of the surgical fastener (200) through a surgical incision (not shown), engagement of the surgically created cavity or joint space (not shown) by the surgical fastener (200) and subsequent rotation of approximately 90 of degrees of cutter (240) relative to an engagement point of the surgically created cavity or joint space by wedge-like tip (220), surgical fastener (200) is positioned to resist pull out of surgical fastener (200) from the surgically created cavity or joint space.

Select preferred embodiments of the current invention have been disclosed and enabled as required by Title 35 of the United States Code.

What is claimed is:

1. A surgical fastener comprising:
    a) a wedge-like tip positioned at a first lengthwise end of a cutter; the wedge-like tip integral with the cutter and of lesser width than the first lengthwise end of the cutter leaving portions of a planar surface of the first lengthwise end conspicuous from the wedge-like tip; the anterior edge of the wedge-like tip parallel to the first lengthwise end of the cutter such that the wedge-like tip is adapted to engage a joint space or a portion of a surgically created cavity or the joint space;
    b) a longitudinal axis (X-X) extending from the wedge-like tip through the cutter and a receiver positioned in a surgeon facing end of the cutter, wherein the receiver is adapted to receive an apparatus distinct from the surgical fastener;
    c) the cutter further comprising a first section and a second section adapted to cut biological tissue; the first and second sections positioned on opposed sides of the longitudinal axis (X-X); each section extending the length of the cutter from the first lengthwise end to the surgeon facing end, wherein the first and second sections are adapted to cut radially relative to the longitudinal axis (X-X);
    d) the first section having a greater width proximate the surgeon facing end; the first section further comprising a slanted first cutting straight edge distal from the longitudinal axis (X-X); the slanted first cutting straight edge slanted at an angle of from about 30 degrees to about 70 degrees relative to the longitudinal axis (X-X); and
    e) the second section having a greater width proximate the surgeon facing end; the second section further comprising a slanted second cutting straight edge distal from the longitudinal axis (X-X); the slanted second cutting straight edge slanted at an angle of from about 30 degrees to about 70 degrees relative to the longitudinal axis (X-X), wherein rotation of the surgical implant connects the surgical implant to the joint space or a portion of the surgically created cavity or the joint space.

2. The surgical fastener of claim 1, wherein each slanted first cutting straight edge comprises first cutting faces and second cutting faces; the cutting faces adapted to cut in clockwise or counterclockwise directions or both directions.

3. The surgical fastener of claim 2, wherein the frontal edge of the wedge-like tip can be either dull, sharp or a combination thereof.

4. The surgical fastener of claim 3, wherein each section of the cutter (240) comprises one or more apertures.

5. The surgical fastener of claim 4, wherein after insertion through a surgical incision, engagement of the joint space or a portion of the surgically created cavity or the joint space by the surgical fastener and subsequent rotation of approximately 90 of degrees of the cutter relative to an engagement point of the wedge-like tip, the surgical fastener is positioned to resist pull out of the surgical fastener from the joint space or a portion of the surgically created cavity or the joint space.

6. A surgical fastener comprising:
    a) a wedge-like tip positioned at a first lengthwise end of a cutter; the wedge-like tip integral with the cutter and of lesser width than the first lengthwise end of the cutter leaving portions of a planar surface of the first lengthwise end conspicuous from the wedge-like tip; the anterior edge of the wedge-like tip parallel to the first lengthwise end of the cutter such that the wedge-like tip is adapted to engage a joint space or a portion of a surgically created cavity or the joint space;
b) a longitudinal axis (X-X) extending from the wedge-like tip through the cutter and a head connected with a surgeon facing end of the cutter, wherein the head is adapted to receive an apparatus distinct from the surgical fastener;
c) the cutter further comprising a first section and a second section adapted to cut biological tissue; the first and second sections positioned on opposed sides of the longitudinal axis (X-X); each section extending the length of the cutter from the first lengthwise end to the surgeon facing end, wherein the first and second sections are adapted to cut radially relative to the longitudinal axis (X-X);
d) the first section having a greater width proximate the surgeon facing end; the first section further comprising a slanted first cutting straight edge distal from the longitudinal axis (X-X); the slanted first cutting straight edge slanted at an angle of from about 30 degrees to about 70 degrees relative to the longitudinal axis (X-X); and
e) the second section having a greater width proximate the surgeon facing end; the second section further comprising a slanted second cutting straight edge distal from the longitudinal axis (X-X); the slanted second cutting straight edge slanted at an angle of from about 30 degrees to about 70 degrees relative to the longitudinal axis (X-X), wherein rotation of the surgical implant connects the surgical implant to the joint space or a portion of the surgically created cavity or the joint space.

7. The surgical fastener of claim 6, wherein the head is a polyaxial head.

8. The surgical fastener of claim 7, wherein each slanted first cutting straight edge comprises first cutting faces and second cutting faces; the cutting faces adapted to cut in clockwise or counterclockwise directions or both directions.

9. The surgical fastener of claim 8, wherein the frontal edge of the wedge-like tip can be either dull, sharp or a combination thereof.

10. The surgical fastener of claim 9 comprising an extender segment extending from surgeon facing end of cutter and connected with the polyaxial head for expanding the multiplanar range of motion of the polyaxial head.

11. The surgical fastener of claim 10, wherein each section of the cutter comprises one or more apertures.

12. The surgical fastener of claim 11, wherein after insertion through a surgical incision, engagement of the joint space or a portion of the surgically created cavity or the joint space by the surgical fastener and subsequent rotation of approximately 90 of degrees of the cutter relative to an engagement point of the wedge-like tip, the surgical fastener is positioned to resist pull out of the surgical fastener from the joint space or a portion of the surgically created cavity or the joint space.

13. A surgical fastener comprising:
a) a wedge-like tip positioned at a first lengthwise end of a cutter; the wedge-like tip integral with the cutter and of lesser width than the first lengthwise end of the cutter, leaving portions of a planar surface of the first lengthwise end conspicuous from the wedge-like tip, such that the wedge-like tip is adapted to engage a joint space or a portion of a surgically created cavity or the joint space;
b) a longitudinal axis (X-X) extending through the wedge-like tip, the anterior edge and a surgeon facing end of the cutter;
c) the cutter further comprising a first section and a second section adapted to cut biological tissue; the first and second sections positioned on opposed sides of the longitudinal axis (X-X); each section extending the length of the cutter from the first lengthwise end to the surgeon facing end, wherein the first and second sections are adapted to cut radially relative to the longitudinal axis (X-X);
d) the first section comprising a greater width proximate the surgeon facing end and a slanted first cutting straight edge distal from the longitudinal axis (X-X) slanted at an angle of from about 30 degrees to about 70 degrees relative to the longitudinal axis (X-X); and
e) the second section comprising a greater width proximate the surgeon facing end and a slanted second cutting straight edge distal from the longitudinal axis (X-X) slanted at an angle of from about 30 degrees to about 70 degrees relative to the longitudinal axis (X-X), wherein after insertion through a surgical incision, engagement of the joint space or a portion of the surgically created cavity or the joint space by the surgical fastener and subsequent rotation of approximately 90 degrees of the cutter relative to an engagement point of the wedge-like tip, the surgeon facing end of the surgical fastener is positioned to resist pull out of the surgical fastener from the joint space or a portion of the surgically created cavity or the joint space.

14. The surgical fastener of claim 13, wherein the frontal edge of the wedge-like tip can be either dull, sharp or a combination thereof.

15. The surgical fastener of claim 14, wherein each slanted first cutting straight edge comprises first cutting faces and second cutting faces; the cutting faces adapted to cut in clockwise or counterclockwise directions or both directions.

16. The surgical fastener of claim 15 comprising a receiver positioned in a surgeon facing end of the cutter.

17. The surgical fastener of claim 15 comprising a head connected with a surgeon facing end of the cutter.

18. The surgical fastener of claim 17, wherein the head is a polyaxial head.

19. The surgical fastener of claim 18 comprising an extender segment extending from surgeon facing end of cutter and connected with the polyaxial head for expanding the multiplanar range of motion of the polyaxial head.

\* \* \* \* \*